US008805049B2

(12) United States Patent
Chan et al.

(10) Patent No.: US 8,805,049 B2
(45) Date of Patent: *Aug. 12, 2014

(54) REDUCING FALSE POSITIVES IN COMPUTER-AIDED DETECTION

(75) Inventors: Paul Chan, Sunnyvale, CA (US); Keith W. Hartman, Redwood City, CA (US)

(73) Assignee: Hologic, Inc., Marlborough, MA (US)

( * ) Notice: Subject to any disclaimer, the term of this patent is extended or adjusted under 35 U.S.C. 154(b) by 194 days.

This patent is subject to a terminal disclaimer.

(21) Appl. No.: 13/451,302

(22) Filed: Apr. 19, 2012

(65) Prior Publication Data

US 2012/0201444 A1 Aug. 9, 2012

Related U.S. Application Data

(63) Continuation of application No. 12/276,300, filed on Nov. 21, 2008, now Pat. No. 8,175,367.

(60) Provisional application No. 60/989,917, filed on Nov. 23, 2007.

(51) Int. Cl.
*A61B 6/03* (2006.01)
*A61B 6/00* (2006.01)

(52) U.S. Cl.
CPC ..................................... *A61B 6/502* (2013.01)
USPC ............................................. 382/132; 378/37

(58) Field of Classification Search
CPC ........ A61B 6/03; A61B 6/502; A61B 8/0825; A61B 5/7267; A61B 5/4312; G06T 2207/30068; G06T 2207/30096; G06T 2207/22084; G06F 19/345; Y10S 128/92; G06N 3/02
USPC ................................................. 382/128–132
See application file for complete search history.

(56) References Cited

U.S. PATENT DOCUMENTS

| 5,627,907 A | 5/1997 | Gur et al. |
| 5,838,815 A | 11/1998 | Gur et al. |

(Continued)

OTHER PUBLICATIONS

Kim, J.K., et al., "Reproducibility of Computer-Aided Detection Marks in Digital Mammography," Korean J Radiol 8(3), Jun. 2007, pp. 198-205.

(Continued)

*Primary Examiner* — Toan Ton
*Assistant Examiner* — John Corbett
(74) *Attorney, Agent, or Firm* — Vista IP Law Group LLP

(57) ABSTRACT

Methods, systems, and related computer program products for computer-aided detection (CAD) of anatomical abnormalities in digital (or digitized) x-ray mammograms are described. The inventive techniques are based on using a foundational CAD processing algorithm that is characterized by at least one of non-shift-invariance, non-rotational-invariance, and non-inversional-invariance. According to one preferred embodiment, a first x-ray mammogram image of a breast is received, and at least one altered version thereof is generated that differs therefrom by at least one of image shift, image rotation, and image inversion. The first x-ray mammogram image and each of the at least one altered versions thereof are individually processed using the foundational CAD algorithm to generate a respective plurality of individual CAD detection sets. The plurality of CAD detection sets are then compared to generate an overall CAD detection set.

16 Claims, 4 Drawing Sheets

(56) References Cited

U.S. PATENT DOCUMENTS

| | | | |
|---|---|---|---|
| 6,067,372 | A | 5/2000 | Gur et al. |
| 6,091,841 | A * | 7/2000 | Rogers et al. .................. 382/132 |
| 6,125,194 | A | 9/2000 | Yeh et al. |
| 6,553,356 | B1 | 4/2003 | Good et al. |
| 6,683,973 | B2 | 1/2004 | Li et al. |
| 8,175,367 | B2 * | 5/2012 | Chan et al. .................... 382/132 |
| 2009/0129656 | A1 * | 5/2009 | Filatov et al. ................. 382/132 |

OTHER PUBLICATIONS

Zheng et al., "A Method to Test the Reproducibility and to Improve Performance of Computer-Aided Detection Schemes for Digitized Mammograms," 2004, Medical Physics, vol. 31, No. 11, pp. 2964-2972.

Taylor et al., "Reproducibility of Prompts in Computer-Aided Detection (CAD) of Breast Cancer," 2003, Clinical Radiology, vol. 58, pp. 733-738.

* cited by examiner

REDUCING FALSE POSITIVES IN COMPUTER-AIDED DETECTION

CROSS-REFERENCE TO RELATED APPLICATIONS

This patent application is a continuation of U.S. patent application Ser. No. 12/276,300, filed Nov. 21, 2008, which claims the benefit of U.S. Provisional Application Ser. No. 60/989,917, filed Nov. 23, 2007. The foregoing applications are each hereby incorporated by reference into the present application in their entirety.

FIELD

This patent specification relates to medical imaging. More particularly, this patent specification relates to the computer-aided detection of anatomical abnormalities in medical imaging, with particular advantageous application to x-ray mammography.

BACKGROUND

The term computer-aided detection (CAD) is commonly used to refer to the use of computers to analyze medical images to detect anatomical abnormalities therein, and/or the use of computers to otherwise process image information in a manner that facilitates perception of the medical image information by a radiologist. Sometimes used interchangeably with the term computer-aided detection are the terms computer-aided diagnosis, computer-assisted diagnosis, or computer-assisted detection. In an abnormality detection context, a CAD algorithm usually identifies a preliminary set of candidate detections in a medical image and then selects which ones, if any, will qualify as actual CAD detections based on a variety of computed features associated with the candidate detections. The CAD results, i.e., the body of information associated with the operation of the CAD algorithm on the medical image, are most often communicated in the form of annotation maps comprising graphical annotations (CAD markers) overlaid on a diagnostic-quality or reduced-resolution version of the medical image, one CAD marker for each CAD detection. Substantial effort and attention has been directed to improving the performance capabilities of CAD systems.

One issue arising in CAD systems relates to their false positive rate, i.e., the percentage of CAD markers displayed to the radiologist that do not actually correspond to truly suspicious or diseased locations. One proposed method for false positive reduction is proposed U.S. Pat. No. 6,067,372 (Gur, et. al.), which is incorporated by reference herein, but is believed to bring about one or more disadvantages and/or to contain one or more shortcomings that are overcome by one or more of the techniques described hereinbelow. Other issues arise as would be apparent to one skilled in the art upon reading the present disclosure.

SUMMARY

Provided in accordance with the preferred embodiments are methods, systems, and related computer program products for computer-aided detection (CAD) of anatomical abnormalities in digital (or digitized) x-ray mammograms. The inventive techniques are based on using a foundational CAD processing algorithm that is characterized by at least one of non-shift-invariance, non-rotational-invariance, and non-inversional-invariance. According to one preferred embodiment, a first x-ray mammogram image of a breast is received, and at least one altered version thereof is generated that differs therefrom by at least one of image shift, image rotation, and image inversion. The first x-ray mammogram image and each of the at least one altered versions thereof are individually processed using the foundational CAD algorithm to generate a respective plurality of individual CAD detection sets. The plurality of CAD detection sets are then compared to generate an overall CAD detection set. Any particular breast location that is identified for CAD marking in at least one of the CAD detection sets is re-evaluated based on a collective evaluation of outcomes for that breast location in all of the CAD detection sets. In one example, this collective evaluation involves a voting technique, although the scope of the preferred embodiments is not so limited.

DETAILED DESCRIPTION

Figure 1:
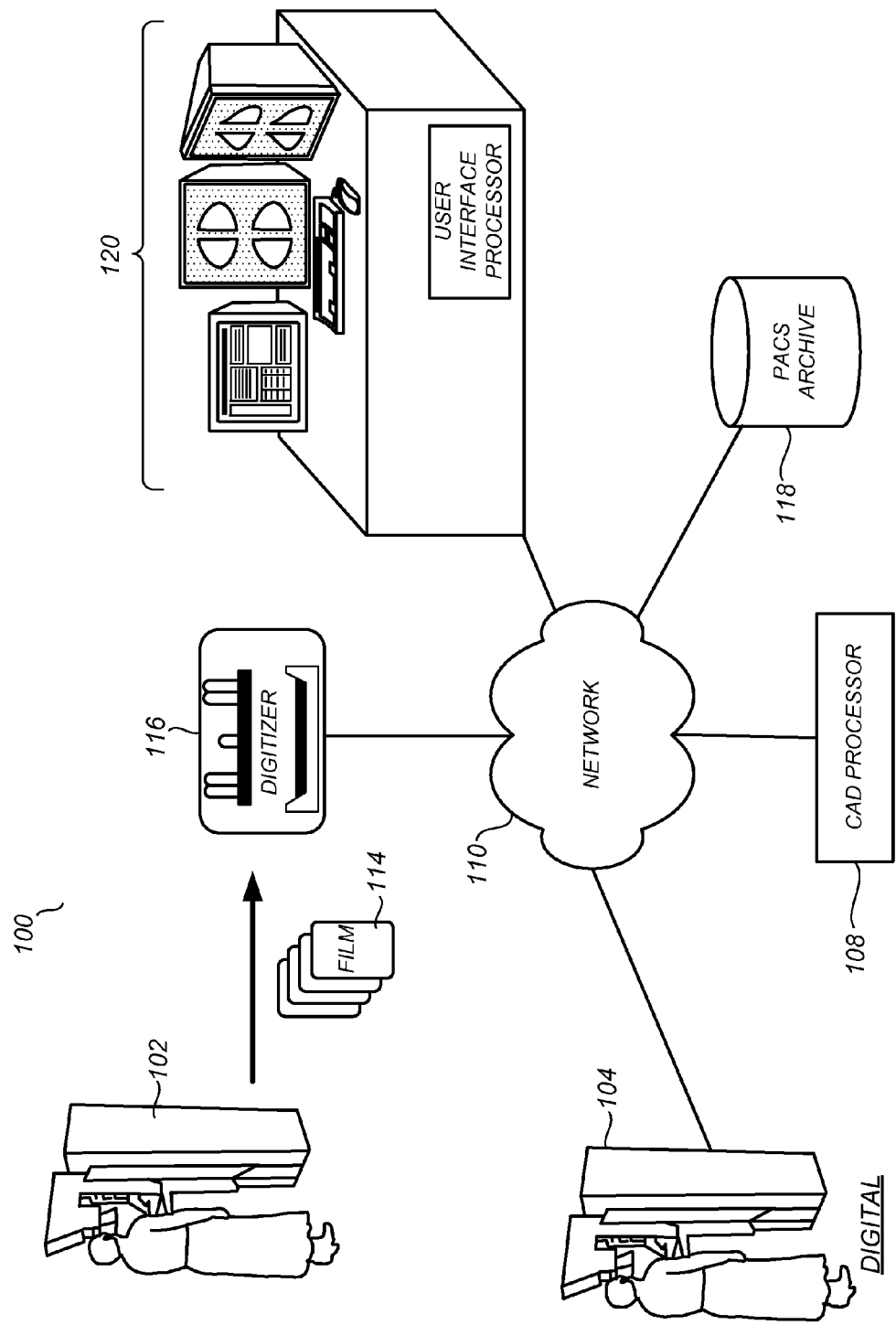
FIG. 1 illustrates a conceptual diagram of a medical imaging environment in which one or more of the preferred embodiments is applicable.

FIG. 1 illustrates a conceptual diagram of a medical imaging environment for which one or more of the preferred embodiments is particularly suited. Methods according to the preferred embodiments are applicable for digital/digitized mammograms acquired using either film-based detectors or digital detectors. Shown in FIG. 1 is a network 110, which may be a HIS/RIS (Hospital Information System/Radiology Information System) network, to which is coupled a film mammogram acquisition device 102 and a digital mammogram acquisition device 104. Film mammograms 114, which are commonly 18×24 cm or 24×30 cm in size, are digitized by a digitizer 116 having a resolution between about 25 µm to 100 µm per pixel depending on type and/or settings. By way of example, a DigitalNow™ digitizer system from R2 Technology (A Hologic Company) of Santa Clara, Calif. digitizes at 50 µm per pixel resolution. The digital acquisition system 104 can be one of many different commercially available systems, each of which often has its own unique digital detector sizes and resolutions. For example, the GE Senographe may use a 24×31 cm detector size or a 19×23 cm detector size, each having detector pixel resolutions of 100 µm. A Hologic Selenia or Siemens Novation system may use a 23 cm×29 cm detector size with a 70 µm per pixel resolution. A Fischer Senoscan may use a 21×29 cm detector having a 25 µm or 50 µm resolution.

A CAD processor 108 coupled to the network 110 receives digital versions of the digital or digitized mammograms and processes them to detect anatomical abnormalities therein. The medical images are then viewed at a softcopy review workstation 120 that offers CAD-assisted viewing. Also coupled to the network 110 is a PACS (Picture Archiving and Communication System) archive 118, generally representing a repository for medical information associated with the medical imaging environment, including both current and archived images, current and archived CAD results, radiology reports for completed cases, and so forth. Preferably, the various medical images and related information are communicated according to the DICOM (Digital Imaging and Communications in Medicine) standard and the network 110 supports the TCP/IP protocol, which is used as the transport protocol for the DICOM standard.

Figure 2:
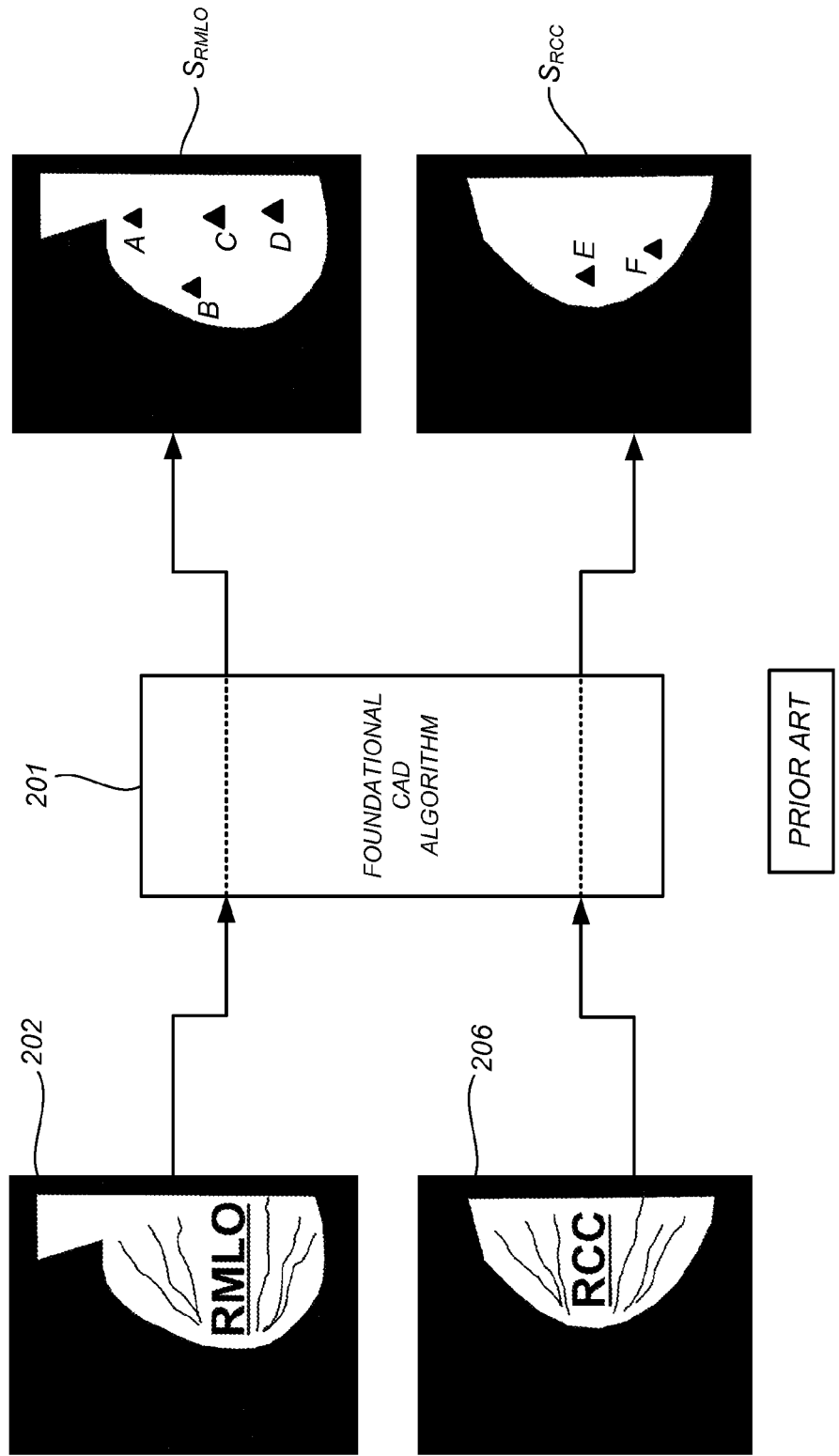
FIG. 2 illustrates conventional computer-aided detection (CAD) in x-ray mammography.

FIG. 2 illustrates conventional computer-aided detection (CAD) in x-ray mammography that is based on using a foundational CAD algorithm 201. For simplicity and clarity of disclosure, only RMLO and RCC views are represented in the examples herein, it being understood that the disclosed techniques are applicable for any standard or non-standard view of either breast. An input RMLO image 202 destined for CAD processing is processed by the foundational CAD algorithm 201 to yield a CAD detection set $S_{RMLO}$, which comprises CAD detections (e.g. suspicious microcalcification cluster, suspicious mass, suspicious architectural distortion, etc.) at breast locations A, B, C, and D. The CAD detection set $S_{RMLO}$ is illustrated in FIG. 2 in the form of an annotated map superimposed upon the RMLO view, in a manner similar to the way the set would be displayed to the radiologist. Although shown graphically in FIG. 2 and in subsequent preferred embodiments herein, it is to be appreciated that a CAD detection set is not necessarily a graphical entity, but rather a set of information generated from the foundational CAD algorithm that identifies potentially suspicious locations in the mammogram, the type of abnormality that may exist at those locations, and often a set of accompanying characteristics that further describe the abnormalities such as size, spiculatedness, and border contrast (for masses), number of microcalcifications in a cluster (for microcalcifications), degree of suspiciousness, and so forth. Also part of the CAD detection set for any particular candidate location is an ultimate binary (yes/no) decision on whether that location should be marked with a CAD marker, or should not be marked with a CAD marker. Referring again to FIG. 2, an input RCC image 206 destined for CAD processing is also processed by the foundational CAD algorithm 201 to yield a CAD detection set $S_{RCC}$ that includes CAD markers at locations E and F.

As used herein, foundational CAD algorithm refers to a CAD algorithm that, by design or consequence, exhibits one or more of non-shift-invariance, non-rotational-invariance, and non-inversional-invariance. By non-shift-invariance, it is meant that the CAD algorithm is at least partially non-robust against small shifts (between about 1-20 pixels, for example) in the input x-ray mammogram image. By non-robust it is meant that, for a clinically detectable percentage (perhaps about 1 percent or more) of a typical population of x-ray mammogram images, the set of CAD detections for a particular x-ray mammogram image would be altered if that x-ray mammogram image were translated by that small amount. Needless to say, as would be apparent to a person skilled in the art, the non-shift-invariance of a CAD algorithm is not a particularly reassuring characteristic. However, in the real world, many CAD algorithms are designed with many different filters, edge detection routines, segmentation techniques, special cases accommodations, locality-dependent processing techniques (for example, different processing for different distances and/or directions from the chest wall, nipple, and/or skinline), directional morphological filtering and/or search algorithms, etc., such that over their years of development, refinement, training, and re-training, it is not outside the scope of possibility that such non-shift-invariance can be exhibited.

By non-rotational-invariance, it is meant that the CAD algorithm is at least partially non-robust against small rotations (between about minus 5 degrees and plus 5 degrees, for example) in the input x-ray mammogram image, whereby, for a clinically detectable percentage of x-ray mammogram images, the set of CAD detections for a particular x-ray mammogram image would be altered if that x-ray mammogram image were rotated by that small amount. By non-inversional invariance, it is meant that the CAD algorithm is at least partially non-robust against spatial inversions (e.g., mirroring, flipping) of the input x-ray mammogram image with respect to a horizontal or vertical axis, whereby, for a clinically detectable percentage of x-ray mammogram images, the set of CAD detections for a particular x-ray mammogram image would be altered if that x-ray mammogram image were flipped about the horizontal and/or vertical axis. As with non-shift-invariance, neither non-rotational-invariance nor non-inversional-invariance are particularly reassuring characteristics for a CAD algorithm to exhibit. Nevertheless, it is indeed possible for these characteristics to be exhibited in the real world for at least the reasons described above. Even one or more commercially available breast x-ray CAD algorithms on the market today is likely to exhibit at least one of non-shift-invariance, non-rotational-invariance, and non-inversional-invariance. In the latter case, for example, a CAD algorithm may be programmed with a local region growing routine that searches outward in a counter-clockwise spiral from a seed point, where the counterclockwise direction was chosen arbitrarily over the clockwise direction. In such case, the CAD algorithm may indeed exhibit non-inversional-invariance, because the routine would now be effectively searching clockwise instead of counterclockwise from the seed pixel, possibly resulting in a different shape (even if slightly so) when the region has been grown.

The term foundational CAD algorithm is used herein to denote such non-shift-invariant, non-rotationally-invariant, or non-inversionally-invariant to represent the fact that a CAD algorithm may be (a) a pre-existing CAD algorithm or modified/updated version thereof having such characteristic(s) by design or consequence that can be improved by the front-and-back-end treatments described herein, or (b) a new CAD algorithm having such characteristics and that is serving as a "core" algorithm inside a larger overall CAD algorithm operating according to one or more of the preferred embodiments.

Figure 3:
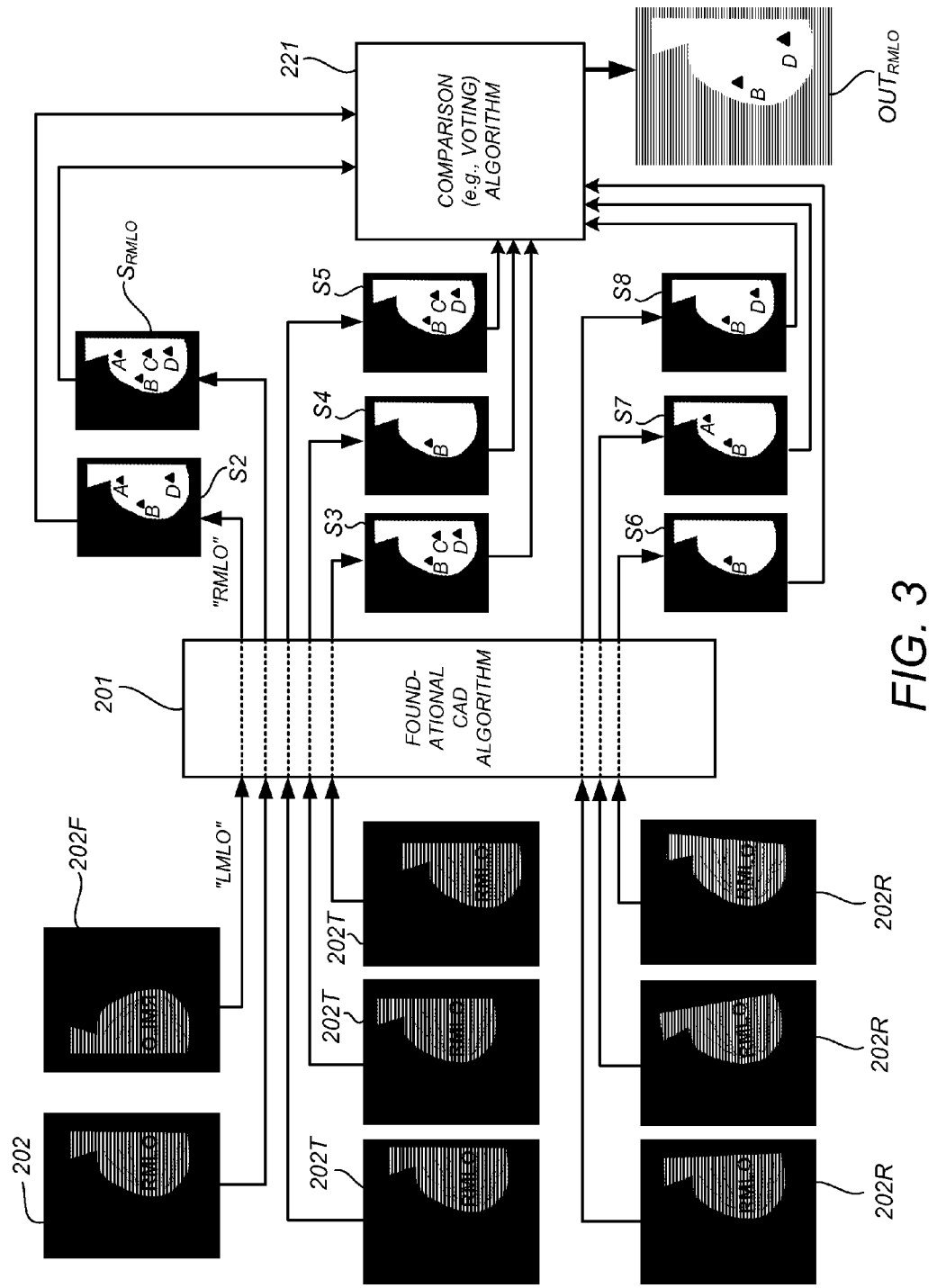
FIG. 3 illustrates CAD in x-ray mammography according to a preferred embodiment.

FIG. 3 illustrates CAD in x-ray mammography according to a preferred embodiment for the RMLO image 202 of FIG. 2, supra. FIG. 3 conceptually illustrates a method for false positive reduction when a foundational CAD processing algorithm 201 is used that is characterized by at least one of non-shift-invariance, non-rotational-invariance, and non-inversional-invariance. As illustrated, at least one altered version of the RMLO image 202 is generated that differs therefrom by at least one of image shift (versions 202T), image rotation (versions 202R), and image inversion 202F. Each of the x-ray mammogram images 202, 202F, 202T, and 202R are individually processed using the foundational CAD algorithm 201 to generate a plurality of corresponding individual CAD detection sets $S_{RMLO}$ and S2-S8. For each altered version, the amount of shifting, rotation, etc. is compensated for (e.g., undone) after the foundational CAD algorithm is completed so that the marked CAD detections are locationally associated with a common reference frame, usually just that of the original input mammogram 202. The plurality of CAD detection sets $S_{RMLO}$ and S2-S8 are then compared using a comparison algorithm 221, such as a voting algorithm, to generate an overall CAD detection set $OUT_{RMLO}$.

The comparison performed by algorithm 221 comprises, for each breast location identified for CAD marking in any of the CAD detection sets $S_{RMLO}$ and S2-S8, making an overall marking decision for that breast location based on a collective evaluation of outcomes for that breast location among all of the CAD detection sets $S_{RMLO}$ and S2-S8. For one preferred embodiment, the collective evaluation comprises a voting technique. For one preferred embodiment, a simple thresholding voting scheme is used, wherein a CAD marker is only maintained if it appears in a threshold percentage (e.g., 70%) of the CAD detection sets.

In one example, there are as few as one altered version of the input x-ray mammogram 202 (e.g., just the flipped version 202F) and the voting is based on just two CAD detection sets. For the particular case of the flipped version 202F, the foundational CAD algorithm needs to be "fooled" (by simple re-identification) into treating the flipped version 202F as an LMLO version, since the algorithm would likely not proceed if it could not find the chest wall on the side that it is expected. In another example, there are at least ten (10) altered versions in various combinations of flip, shift, and rotate, and at least eleven (11) CAD detection sets included in the voting.

Figure 4:
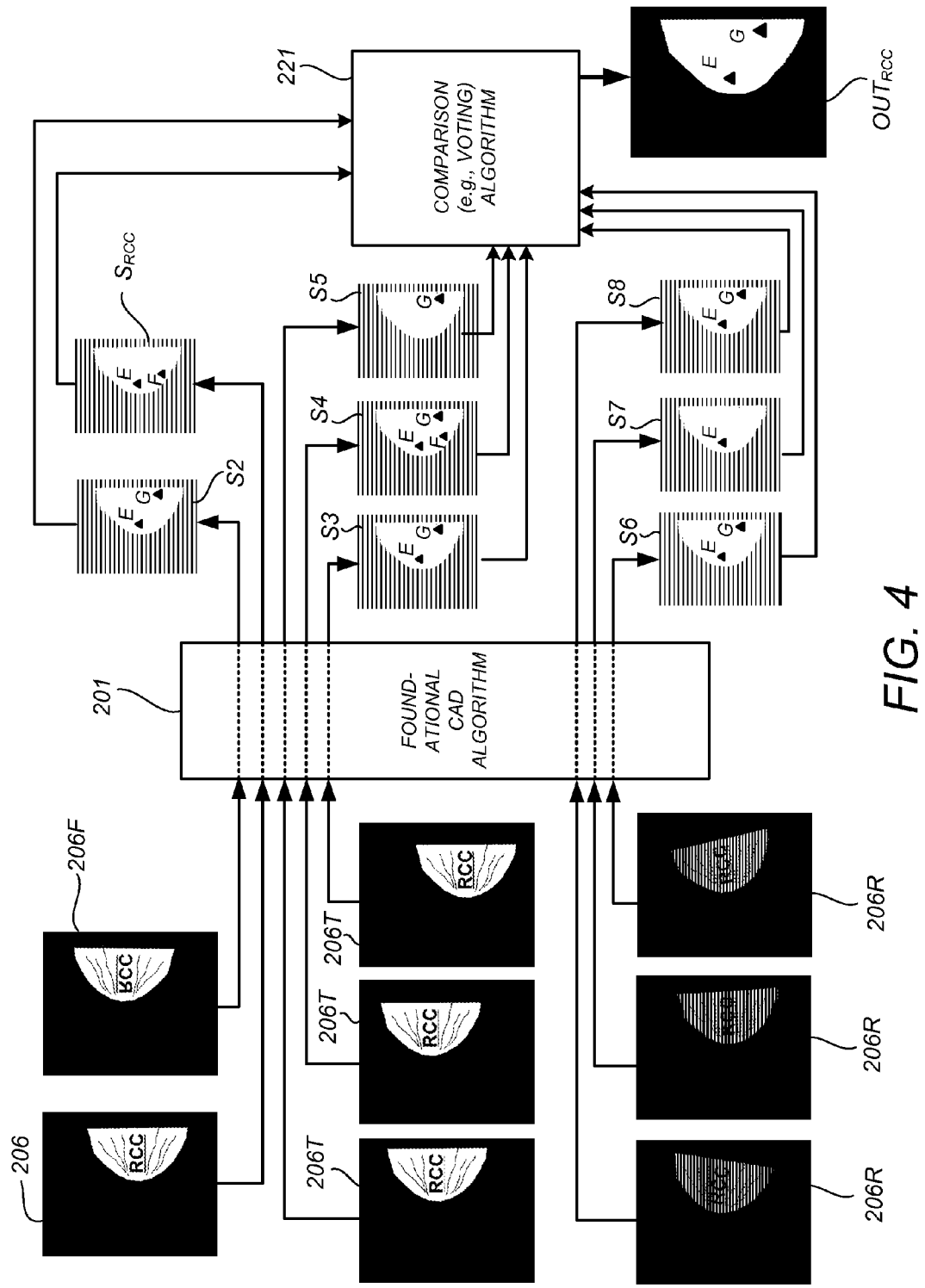
FIG. 4 illustrates CAD in x-ray mammography according to a preferred embodiment.

FIG. 4 illustrates CAD in x-ray mammography according to a preferred embodiment for the RCC image 206 of FIG. 2, supra. The RCC version of the technique proceeds in a manner similar to the RMLO version, based on flipped (206F), translated (206T), and rotated (206R) versions of the input RCC image 206, except that the flipped version 206F is flipped vertically instead of horizontally, as shown.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although described hereinabove in the context of digital and film-based x-ray mammography, one or more of the preferred embodiments are also readily applicable in the context of breast x-ray tomosynthesis. More generally, techniques according to one or more of the preferred embodiments are generally extensible to any imaging modality for which there are underlying foundational CAD algorithms that exhibit at least some degree of non-shift-invariance, non-rotational-invariance, or non-inversional-invariance.

By way of further example, in yet other preferred embodiments, the underlying CAD algorithms are non-deformation-invariant in one or more directions (i.e., non-robust against small stretches or shrinkages along one or more directions) while the altered versions of the input x-ray mammogram are slightly stretched or shrunk versions thereof in one or more directions. Notably, one collateral advantage of techniques according to one or more of the preferred embodiments is that, in addition to false positive reduction, there is also a false negative reduction inherently provided. For example, as illustrated in the example of FIGS. 2 and 4, the foundational CAD algorithm 201 might not identify a particular breast location "G" for CAD marking in the original input x-ray mammogram, but might identify that particular location "G" for CAD marking in a sufficient number of the altered versions of the original input x-ray mammogram such that the location "G" receives a CAD marker in the overall CAD detection set, thereby avoiding a false negative. Therefore, reference to the details of the preferred embodiments are not intended to limit their scope, which is limited only by the scope of the claims set forth below.

What is claimed is:

1. A method for computer-aided detection (CAD) of anatomical abnormalities in x-ray mammograms based on a foundational CAD processing algorithm, the foundational CAD processing algorithm being characterized by at least one of non-shift-invariance, non-rotational-invariance, and non-inversional-invariance, the method comprising:

receiving a first x-ray mammogram image of a breast in digital form;

processing by digital computer the first x-ray mammogram image to generate at least one altered version thereof that differs therefrom by at least one of image shift, image rotation, and image inversion;

individually processing the first x-ray mammogram image and each of the at least one altered versions using the foundational CAD algorithm to generate a respective plurality of individual CAD detection sets; and comparing the plurality of CAD detection sets to generate an overall CAD detection set for the first x-ray mammogram image, wherein the foundational CAD algorithm is non-deformation-invariant in at least one direction.

2. The method of claim 1, wherein comparing comprises, for each location in the breast identified for CAD marking in at least one of the CAD detection sets, including that breast location in the overall CAD detection set based on a collective evaluation of outcomes for that breast location in all of the CAD detection sets.

3. The method of claim 2, wherein the collective evaluation of outcomes for the breast location comprises a voting technique in which the breast location is included in the overall CAD detection set only when at least seventy percent (70%) of the CAD detection sets have identified the breast location for CAD marking, and wherein the method further comprises displaying the overall CAD detection set to a viewer in conjunction with the first x-ray mammogram image on an output display.

4. The method of claim 1, wherein the at least one altered version includes at least ten (10) successively rotated versions of the first x-ray mammogram image having rotation angles distributed between about −5 degrees and 5 degrees.

5. The method of claim 1, the first x-ray mammogram image having a number of pixels in a range of about 1K×1K to about 10K×10K pixels, wherein the at least one altered version includes at least ten (10) successively shifted versions of the first x-ray mammogram image having shift amounts distributed between about 2 pixels and 20 pixels.

6. The method of claim 1, the foundational CAD algorithm exhibits non-shift invariance by being at least partially non-robust against shifts of about 1 to about 20 pixels in the first x-ray mammogram image.

7. The method of claim 1, the foundational CAD algorithm exhibiting non-rotational invariance by being at least partially non-robust against rotations of about −5 degrees to about +5 degrees in the first x-ray mammogram image.

8. The method of claim 1, wherein the first x-ray mammogram is processed to generate a single altered version of the first x-ray mammogram that differs from the first x-ray mammogram image by at least one of image shift, image rotation and image inversion.

9. The method of claim 8, the single altered version being a flipped version relative to the first x-ray mammogram image.

10. The method of claim 1, wherein the foundational CAD algorithm is non-robust against small stretches or shrinkages along at least one direction.

11. A method for computer-aided detection (CAD) of anatomical abnormalities in x-ray mammograms based on a foundational CAD processing algorithm, the foundational CAD processing algorithm being characterized by at least one of non-shift-invariance, non-rotational-invariance, and non-inversional-invariance, the method comprising:

receiving a first x-ray mammogram image of a breast in digital form;

processing by digital computer the first x-ray mammogram image to generate at least one altered version thereof that differs therefrom by at least one of image shift, image rotation, and image inversion;

individually processing the first x-ray mammogram image and each of the at least one altered versions using the foundational CAD algorithm to generate a respective plurality of individual CAD detection sets; and comparing the plurality of CAD detection sets to generate an overall CAD detection set for the first x-ray mammogram image, the foundational CAD algorithm exhibiting non-inversional invariance by being at least partially non-robust against mirroring or flipping spatial inversions of the first x-ray mammogram image.

12. A method for computer-aided detection (CAD) of anatomical abnormalities in x-ray mammograms based on a foundational CAD processing algorithm, the foundational CAD processing algorithm being characterized by non-shift-invariance, nonrotational-invariance, and non-inversional-invariance, the method comprising:

receiving a first x-ray mammogram image of a breast in digital form;

processing by digital computer the first x-ray mammogram image to generate a plurality of altered versions thereof including at least one spatially inverted version thereof, at least one rotated version thereof, and at least one shifted version thereof;

individually processing the first x-ray mammogram image and each of the plurality of altered versions using the foundational CAD algorithm to generate a respective plurality of individual CAD detection sets; and comparing the plurality of CAD detection sets to generate an overall CAD detection set for the first x-ray mammogram image.

13. The method of claim 12, wherein comparing comprises, for each location in the breast identified for CAD marking in at least one of the CAD detection sets, including that breast location in the overall CAD detection set based on a collective evaluation of outcomes for that breast location in all of the CAD detection sets.

14. The method of claim 13, wherein the collective evaluation of outcomes for the breast location comprises a voting technique in which the breast location is included in the overall CAD detection set only when at least seventy percent (70%) of the CAD detection sets have identified the breast location for CAD marking, and wherein the method further comprises displaying the overall CAD detection set to a viewer in conjunction with the first x-ray mammogram image on an output display.

15. The method of claim 12, wherein the at least one rotated version includes at least ten (10) successively rotated versions of the first x-ray mammogram image having rotation angles distributed between about −5 degrees and 5 degrees.

16. The method of claim 12, the first x-ray mammogram image having a number of pixels in a range of about 1K×1K to about 10K×10K pixels, wherein the at least one shifted version includes at least ten (10) successively shifted versions of the first x-ray mammogram image having shift amounts distributed between about 2 pixels and 20 pixels.

* * * * *